(12) United States Patent
Re

(10) Patent No.: US 8,343,161 B2
(45) Date of Patent: Jan. 1, 2013

(54) FEMORAL GUIDE FOR ACL REPAIR HAVING MULTIPLE LUMEN

(75) Inventor: Paul Re, Boston, MA (US)

(73) Assignee: Covidien LP, Mansfield, MA (US)

( * ) Notice: Subject to any disclaimer, the term of this patent is extended or adjusted under 35 U.S.C. 154(b) by 668 days.

(21) Appl. No.: 12/548,791

(22) Filed: Aug. 27, 2009

(65) Prior Publication Data

US 2010/0049201 A1 Feb. 25, 2010

Related U.S. Application Data

(63) Continuation-in-part of application No. 12/366,967, filed on Feb. 6, 2009.

(60) Provisional application No. 61/066,575, filed on Feb. 21, 2008, provisional application No. 61/066,572, filed on Feb. 21, 2008.

(51) Int. Cl.
*A61B 17/58* (2006.01)
(52) U.S. Cl. .......................................................... 606/89
(58) Field of Classification Search ............... 606/96–98, 606/103, 104
See application file for complete search history.

(56) References Cited

U.S. PATENT DOCUMENTS

| | | | |
|---|---|---|---|
| 4,911,153 A | 3/1990 | Border | |
| 5,078,719 A * | 1/1992 | Schreiber | 606/87 |
| 5,147,367 A * | 9/1992 | Ellis | 606/96 |
| 5,152,764 A | 10/1992 | Goble | |
| 5,250,055 A | 10/1993 | Moore et al. | |
| 5,306,278 A * | 4/1994 | Dahl et al. | 606/96 |
| 5,314,429 A | 5/1994 | Goble | |
| 5,320,115 A | 6/1994 | Kenna | |
| 5,320,626 A | 6/1994 | Schmieding | |
| 5,385,567 A | 1/1995 | Goble | |
| 5,445,642 A | 8/1995 | McNulty | |
| 5,514,144 A | 5/1996 | Bolton | |
| 5,520,693 A | 5/1996 | McGuire et al. | |
| 5,562,664 A | 10/1996 | Durlacher et al. | |
| 5,562,669 A | 10/1996 | McGuire | |
| 5,570,706 A | 11/1996 | Howell | |
| 5,613,971 A | 3/1997 | Lower et al. | |
| 5,891,150 A | 4/1999 | Chan | |
| 5,968,050 A | 10/1999 | Torrie | |
| 6,022,356 A | 2/2000 | Noyes et al. | |
| 6,096,038 A * | 8/2000 | Michelson | 606/86 A |
| 6,254,606 B1 | 7/2001 | Carney et al. | |
| 6,309,396 B1 | 10/2001 | Ritland | |

(Continued)

FOREIGN PATENT DOCUMENTS

CA 2654486 8/2009

(Continued)

OTHER PUBLICATIONS

PCT International Search Reports dated Oct. 19, 2010 for the corresponding application PCT/US2010/046764, Oct. 25, 2010 for the corresponding application PCT/US2010/046774, Oct. 26, 2010 for the corresponding application PCT/US2010/046769, and Oct. 27, 2010 for the corresponding application PCT/US2010/046804.

Primary Examiner — Nicholas Woodall

(57) ABSTRACT

A guide for positioning a femoral tunnel during an ACL repair. The device may include a shaft having two or more lumen extending longitudinally therethrough. The device may also include a distal offset projection, at least a portion of the distal offset projection extending distally from the elongated shaft.

10 Claims, 10 Drawing Sheets

U.S. PATENT DOCUMENTS

| | | |
|---|---|---|
| 6,352,538 B2 | 3/2002 | McGuire et al. |
| 6,878,150 B1 | 4/2005 | McGuire et al. |
| 7,025,770 B2 | 4/2006 | McGuire et al. |
| 7,032,599 B2 | 4/2006 | May et al. |
| 7,458,975 B2 | 12/2008 | May et al. |
| 7,491,206 B2 | 2/2009 | Whittaker et al. |
| 2002/0151903 A1 | 10/2002 | Takei et al. |
| 2003/0009173 A1 | 1/2003 | McGuire et al. |
| 2003/0145860 A1* | 8/2003 | Johnson .................... 128/207.15 |
| 2004/0267273 A1 | 12/2004 | Whittaker et al. |
| 2005/0203523 A1 | 9/2005 | Wenstrom et al. |
| 2005/0228399 A1 | 10/2005 | Kubo et al. |
| 2006/0074434 A1 | 4/2006 | Wenstrom, Jr. et al. |
| 2006/0149283 A1 | 7/2006 | May et al. |
| 2006/0293689 A1 | 12/2006 | Miller et al. |
| 2007/0123902 A1 | 5/2007 | Berberich et al. |
| 2007/0191853 A1 | 8/2007 | Stone |
| 2007/0233128 A1 | 10/2007 | Schmieding et al. |
| 2007/0233151 A1 | 10/2007 | Chudik |
| 2008/0103506 A1 | 5/2008 | Volpi et al. |
| 2008/0234819 A1 | 9/2008 | Schmieding et al. |
| 2009/0018654 A1 | 1/2009 | Schmieding et al. |
| 2009/0030417 A1 | 1/2009 | Takahashi |
| 2009/0157081 A1 | 6/2009 | Homan et al. |
| 2009/0187244 A1 | 7/2009 | Dross |
| 2009/0265003 A1 | 10/2009 | Re et al. |

FOREIGN PATENT DOCUMENTS

| | | |
|---|---|---|
| EP | 279129 A1 * | 8/1988 |
| FR | 2744621 | 8/1997 |

* cited by examiner

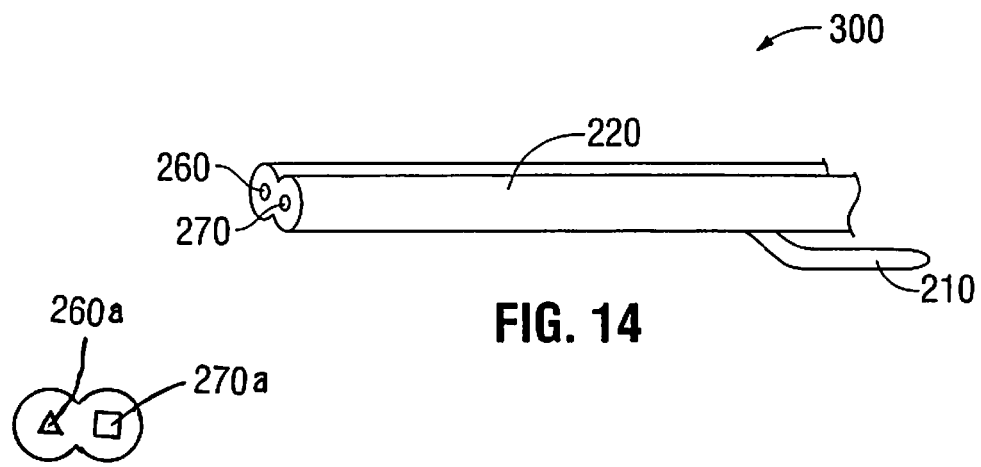
FIG. 14
FIG. 14A
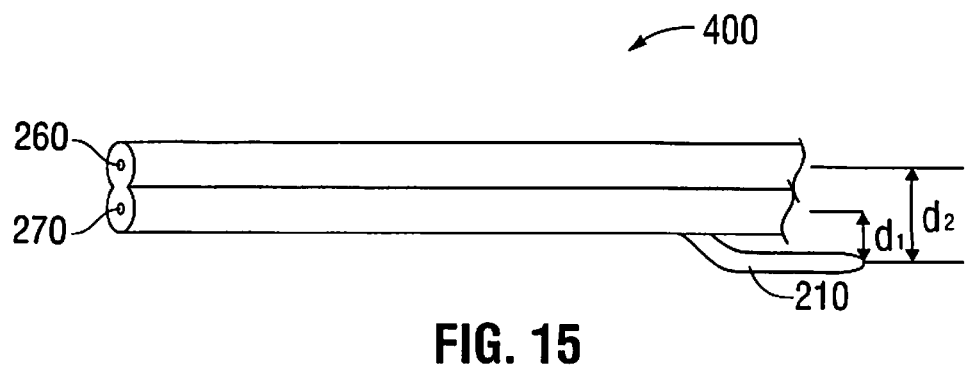
FIG. 15
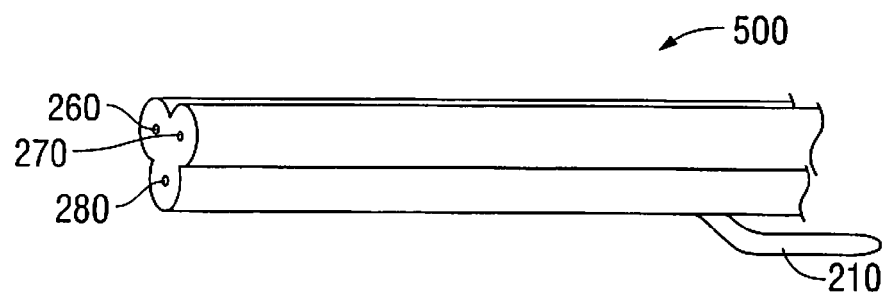
FIG. 16

FEMORAL GUIDE FOR ACL REPAIR HAVING MULTIPLE LUMEN

CROSS REFERENCE TO RELATED APPLICATIONS

This application is a continuation-in part of, and claims the benefit of priority to, U.S. patent application Ser. No. 12/366,967, filed Feb. 6, 2009, entitled "Guide for Creating a Femoral Tunnel During an ACL Reconstruction," and U.S. Provisional Patent Application Ser. No. 61/066,575, filed Feb. 21, 2008, entitled "Guide for Creating a Femoral Tunnel During an ACL Reconstruction," the disclosures of each being incorporated herein by reference in their entirety. In addition, this application is related to U.S. Provisional Patent Application Ser. No. 61/066,572, filed Feb. 21, 2008, entitled "Device for Orienting the Tibial Tunnel Position During an ACL Reconstruction" and U.S. patent application Ser. No. 12/367,007, filed Feb. 6, 2009, entitled "Device for Orienting the Tibial Tunnel Position During an ACL Reconstruction," the disclosures of each also being incorporated herein by reference in their entirety.

BACKGROUND

1. Technical Field

This invention relates to surgical apparatus and procedures in general, and more particularly to surgical apparatus and procedures for reconstructing a ligament.

2. Background of Related Art

A ligament is a piece of fibrous tissue which connects one bone to another. Ligaments are frequently damaged (e.g., detached or torn or ruptured, etc.) as the result of injury and/or accident. A damaged ligament can cause instability, impede proper motion of a joint and cause pain. Various procedures have been developed to repair or replace a damaged ligament. The specific procedure used depends on the particular ligament which is to be restored and on the extent of the damage.

One ligament which is frequently damaged as the result of injury and/or accident is the anterior cruciate ligament (i.e., the ACL). Looking first at FIGS. 1 and 2, it will be seen that the ACL 5 extends between the top of the tibia 10 and the bottom of the femur 15. A damaged ACL can cause instability of the knee joint and cause substantial pain and arthritis. For this reason, ACL reconstruction is a common procedure with more than 100,000 cases being performed in the United States annually.

Various procedures have been developed to restore and/or reconstruct a damaged ACL through a graft ligament replacement. Traditionally, this procedure is performed utilizing a trans-tibial approach. In this approach, a tibial tunnel or bone tunnel 20 is created in tibia 20 by drilling up through tibia 10. Bone tunnel 20 is then used to access an inner surface of femur 15 to drill a bone tunnel 25 up into femur 15. More particularly, once tibial tunnel 20 is created, a conventional femoral guide, often referred to as an "over-the-top" guide (FIG. 4), is used to accurately locate the femoral tunnel 25. More specifically, the "over-the-top" guide is placed through the tibial tunnel, across the joint, through the femoral notch, and then into position so that the distal finger of the guide is positioned against the backside of the femur. (FIG. 5). Proper placement of the femoral tunnel is imperative in order for the ACL graft to be properly positioned on the femur. However, as a result of using the aforementioned trans-tibial technique and the aforementioned conventional "over-the-top" femoral guide, the position of the femoral tunnel is effectively dictated by the position of the first-drilled tibial tunnel. This often results in a femoral tunnel position, and thus, an ACL reconstruction (i.e., graft orientation, etc.) that is less than optimal.

In an attempt to better position the femoral tunnel, surgeons have recently begun utilizing the so-called "medial portal technique" to drill and create the femoral tunnel. By drilling the femoral tunnel through the medial portal or an accessory portal, the femoral and tibial tunnels may be drilled independently of one another and, therefore, in a more appropriate anatomical position.

As shown in FIG. 6, when drilling the femoral tunnel through the medial portal, surgeons typically still use the same "over-the-top" femoral guide used during the aforementioned trans-tibial approach. However, because the "over-the-top" femoral guide is designed for use in a trans-tibial approach, the "over-the-top" femoral guide is not ideal for use in a medial portal approach. These "over-the-top" femoral guides generally have narrow-shaped distal tip geometries to aid in their ability to pass through the tibial tunnel. In addition, such femoral guides have an offset spatula design to hook the posterior femoral notch, thereby aiding in positioning of the guide. Aside from this spatula design, these femoral guides have no other specific referencing geometries for properly positioning the femoral tunnel.

Traditionally, surgeons utilize what is known as a "clock face" orientation in order to decide where to place the femoral tunnel within the notch of knee. This clock face orientation technique designates positions along the notch from 9 o'clock to 3 o'clock, depending on which knee is being reconstructed. This technique, while seemingly simplistic, is limited by a number of factors, one being that the positioning of the imaginary clock face along the notch is completely subjective and hence widely affected by the specific implementation of the surgeon. Therefore, it would be beneficial to have a femoral guide for use in medial approach ACL reconstruction surgery that is configured for more accurate femoral tunnel positioning. In addition, it would be beneficial if the femoral guide is designed in such a way that it might also be utilized during a trans-tibial approach.

SUMMARY

A guide for positioning a guide wire on a femur to allow a tunnel to be formed in the femur along the guide wire is provided. The guide includes an elongated shaft having proximal and distal ends, and a distal tip formed on the distal end of the elongated shaft, the distal tip having a diameter substantially similar in size to the diameter of the desired resultant femoral tunnel, wherein the elongated shaft and the distal tip are cannulated to receive the guide wire.

The distal tip further may further include at least one of opposed fingers and a distal projection. The opposed fingers or distal projection may be configured to reference a leading edge of the posterior cruciate ligament. The opposed fingers or distal projections may further be configured to reference a posterior femoral cortex. The elongated shaft may be configured to extend across a knee joint, the length of a tibial tunnel, or out of a medial port. The distal end may include a substantially circular cross-section, a substantial semi-spherical cross-section, or an unroofed cross-section.

Additionally, there is provided a method of positioning a femoral tunnel during an ACL reconstruction. The method includes the steps of providing a femoral guide including an elongated shaft having a distal end, the distal end including a diameter substantially similar in size to the diameter of the desired resultant femoral tunnel, wherein the elongated shaft and the distal end are cannulated to receive a guide wire therethrough, inserting the femoral guide into a knee joint, positioning the distal end of the guide against the femur, and inserting the guide wire through the femoral guide and into the femur.

The femoral guide may include one of opposed fingers and a distal projection configured for referencing a posterior cruciate ligament. The method may further include the step of referencing a leading edge of a posterior cruciate ligament and/or the posterior femoral cortex. The method may also include the step of flexing the knee to 120 degrees. The femoral guide may be inserted into the knee joint using a medial portal approach or a trans-tibial approach.

In accordance with various embodiments, the present invention may provide a device for positioning a femoral tunnel during ACL reconstruction, the device comprising a shaft defining at least two lumen extending longitudinally therethrough, each lumen configured to receive a guide wire therethrough. The device may also include a distal offset projection, at least a portion of the distal offset projection extending distally from the elongated shaft. The first lumen and the second lumen may be arranged side-by-side relative to each other. A centerline of the first lumen may be disposed at a distance from a distal offset projection that is equal to a distance between a centerline of the second lumen and the distal offset projection. The first lumen and the second lumen may be arranged vertically relative to each other. A centerline of the first lumen may be disposed at a distance $d_1$ from a distal offset projection that is not equal to a distance $d_2$ between a centerline of the second lumen and the distal offset projection. The difference between distance $d_1$ and distance $d_2$ may be in the range from 0 to about 4 mm. The first lumen may have a size that is different from a size of the second lumen. Additionally or alternatively, the first lumen may have a cross-sectional shape that is different from a cross-sectional shape of the second lumen. Any number of lumen may be provided, e.g., three or more.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 14 is a perspective view of a femoral tunnel positioning guide according to another embodiment of the present disclosure;

FIG. 14a is an end view of an alternative embodiment of the present disclosure, showing first and second lumen having different cross-sectional shapes and sizes;

FIG. 15 is a side view of the femoral tunnel positioning guide according to another embodiment of the present disclosure; and FIG. 16 is a front view of the femoral tunnel positioning guide according to another embodiment of the present disclosure.

DETAILED DESCRIPTION OF THE EMBODIMENTS

Figure 1:
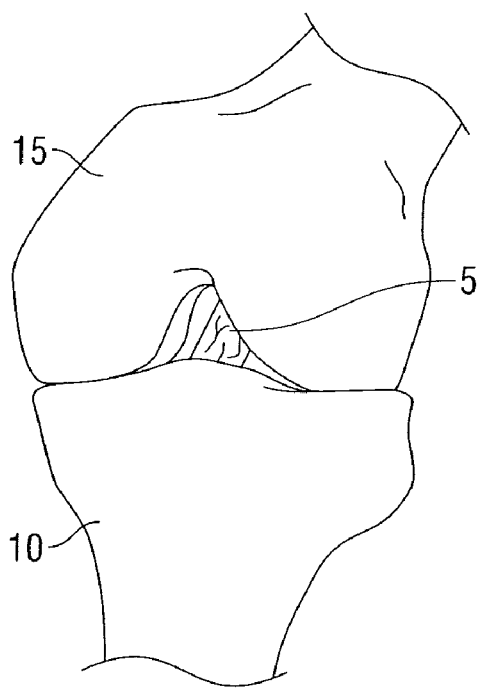
FIG. 1 is a perspective view of a knee joint showing an ACL.
Figure 2:
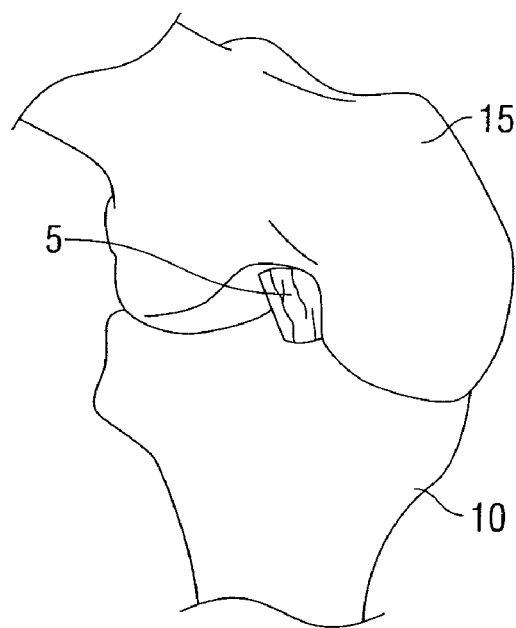
FIG. 2 is an alternate perspective view of the knee joint of FIG. 1.
Figure 3:
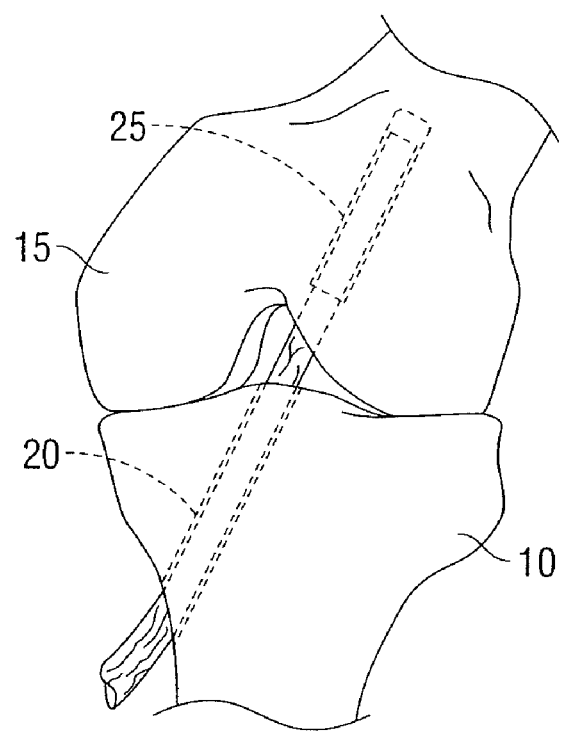
FIG. 3 is a perspective view of a knee joint including tibial and femoral tunnels (shown in phantom) and a ligament graft.
Figure 4:
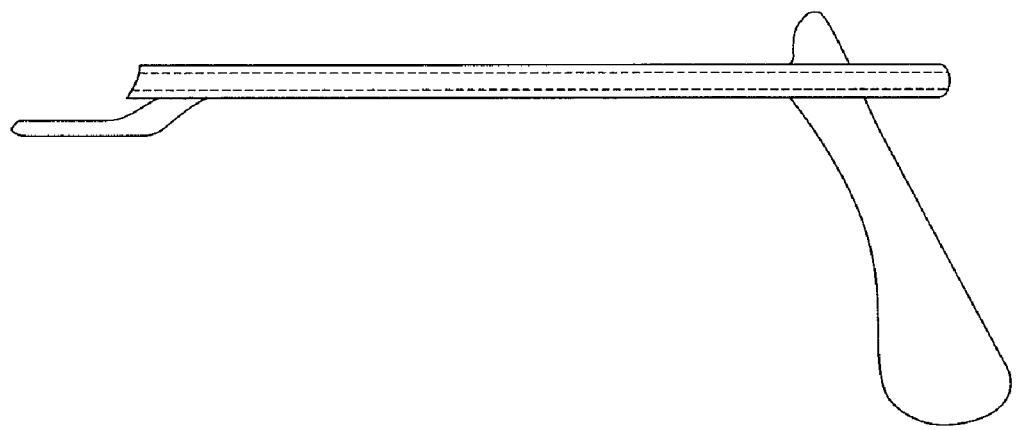
FIG. 4 is a side view of a conventional "over-the-top" femoral guide.
Figure 5:
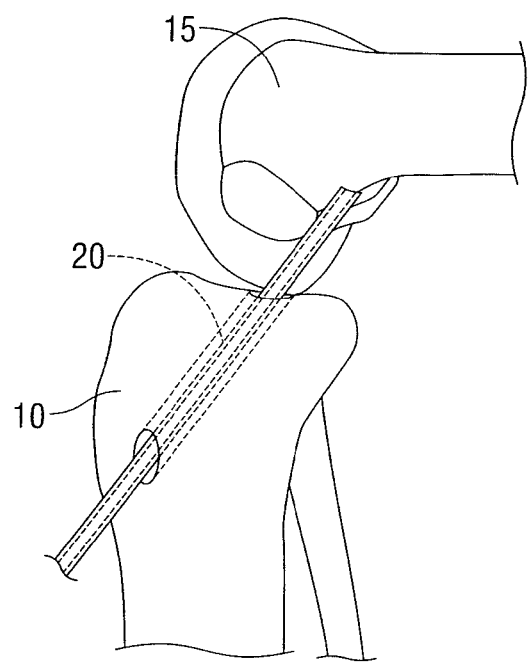
FIG. 5 is side view of a knee joint including the "over-the-top" femoral guide of FIG. 4 accessing the femur using the trans-tibial approach.
Figure 6:
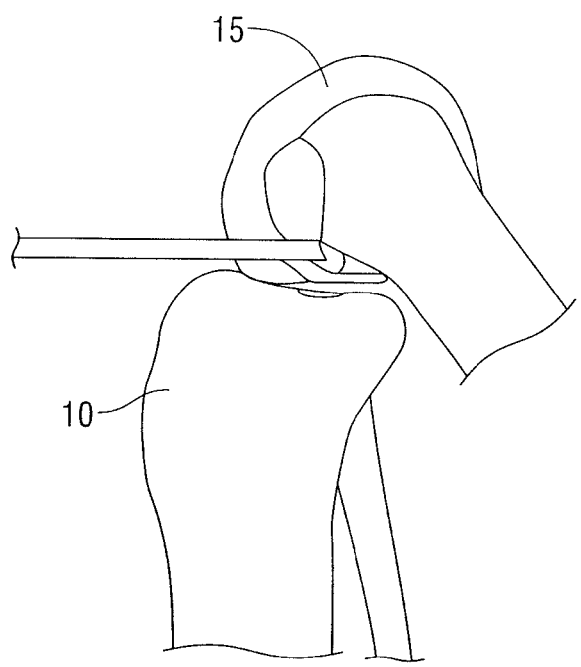
FIG. 6 is a side view of a knee joint including the "over-the-top" femoral guide of FIG. 4 access the femur using the medial portal approach.
Figure 7A:
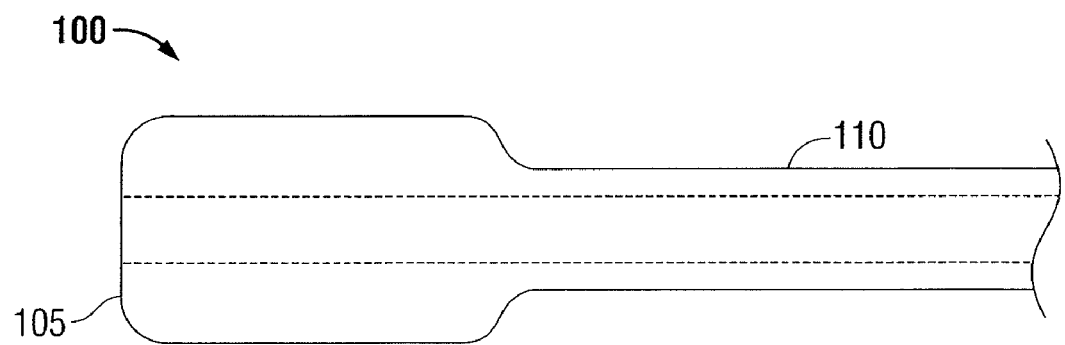
FIGS. 7A-7C are side views of the distal end of various embodiments of a femoral guide according to the present disclosure.
Figure 7B:
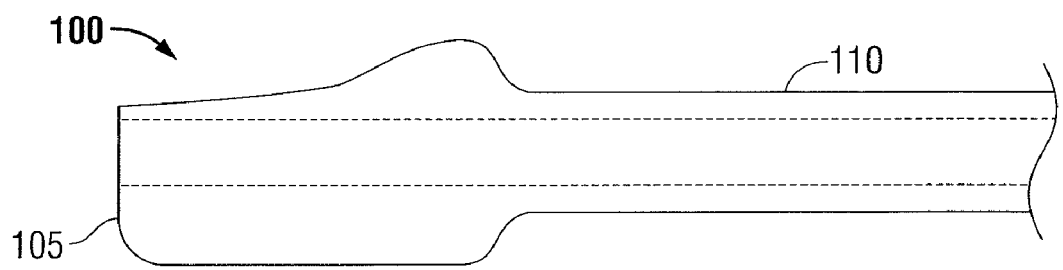
Figure 7C:
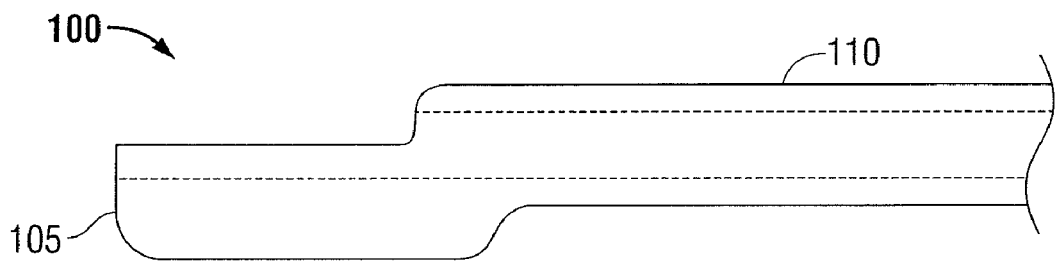
Figure 8A:
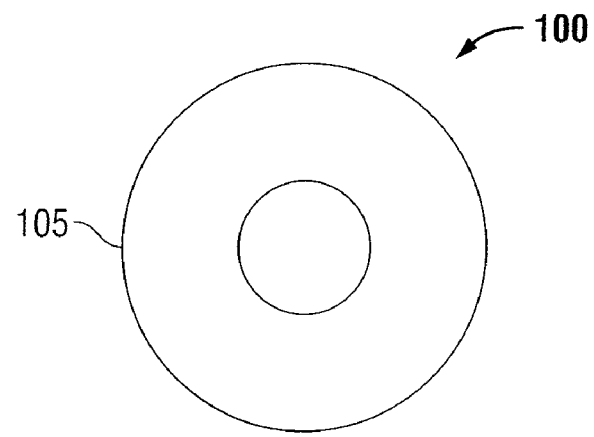
FIGS. 8A-8C are end views of the distal end of the embodiments of FIGS. 7A-7C, respectively.
Figure 8B:
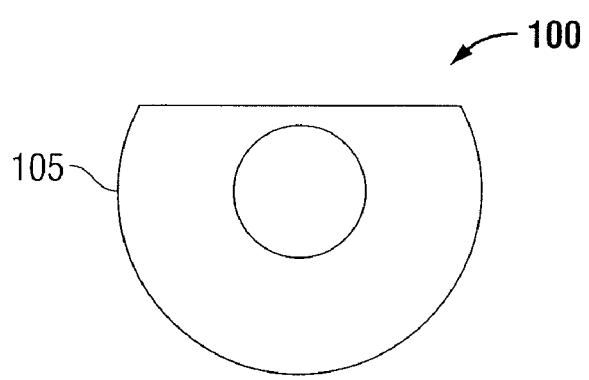
Figure 8C:
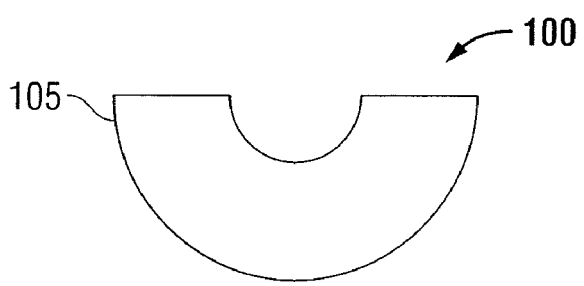
Figure 9A:
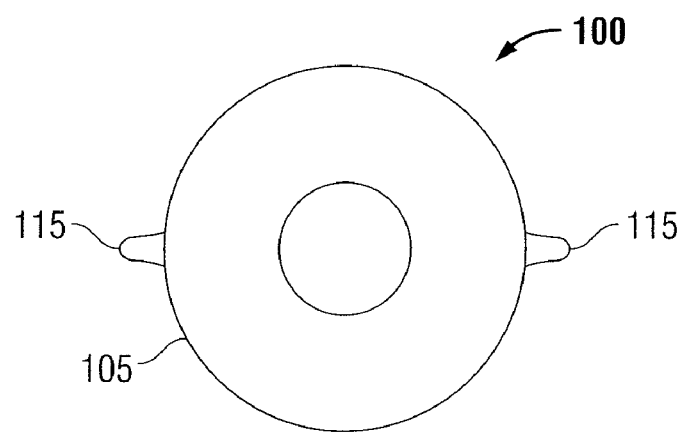
FIGS. 9A-9C are end views of the distal end of alternative embodiments of a femoral guide according to the present disclosure.
Figure 9B:
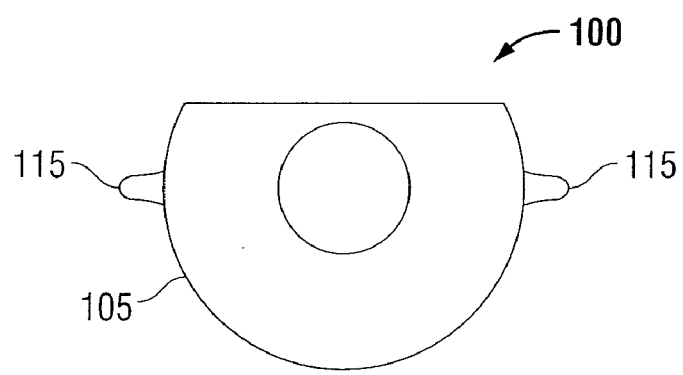
Figure 9C:
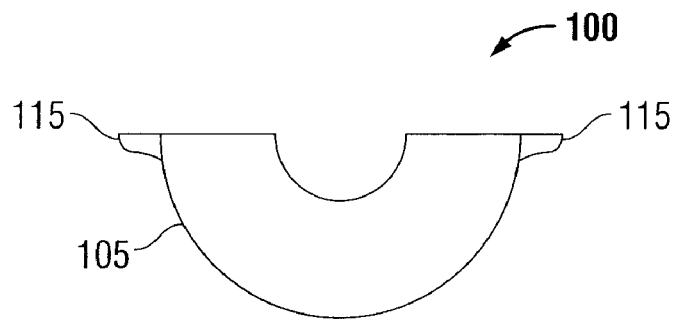
Figure 10A:
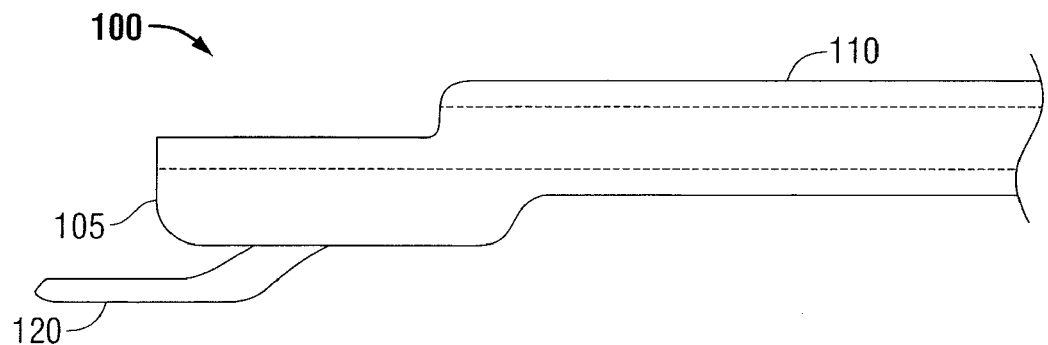
FIG. 10A is a side view of a distal end of a femoral guide according to another embodiment of the present disclosure.
Figure 10B:
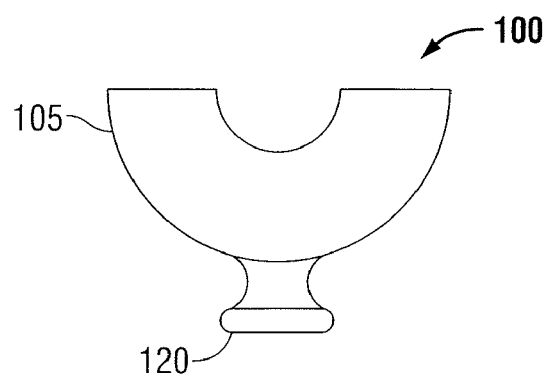
FIG. 10B is an end view of the distal end of the femoral guide of FIG. 10A.
Figure 10C:
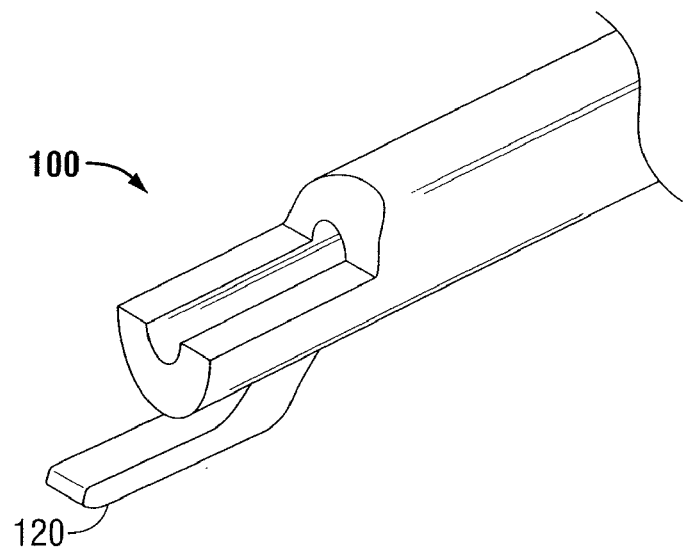
FIG. 10C is a side view of the femoral guide of FIGS. 10A and 10B.
Figure 10D:
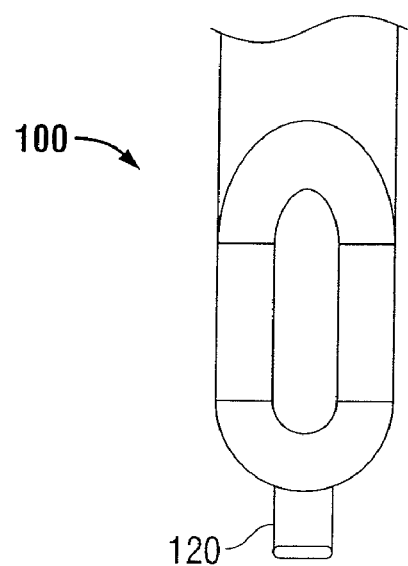
FIG. 10D is an end view of the femoral guide of FIGS. 10A-10C.
Figure 10E:
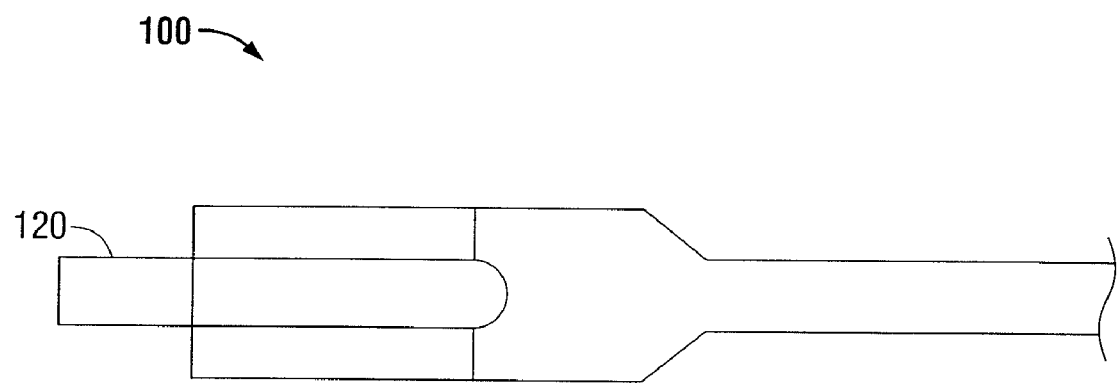
FIG. 10E is top view of the distal end of the femoral guide of FIGS. 10A-10D.

The femoral guide of the present disclosure is designed to be used in determining the position of a femoral tunnel guide wire which facilitates the positioning of a femoral tunnel during an ACL reconstruction. As with conventional femoral guides, the femoral guide of the present disclosure may reference an "over-the-top" position with an offset spatula; however, it can also be designed and utilized without such an offset spatula. This includes having no spatula, or instead having one or multiple spike projections or other similar projections to hold the spatula in position on the bone.

FIGS. 7A-10E show various embodiments of a femoral guide 100 formed in accordance with the present disclosure. Femoral guide 100 generally includes a distal tip 105 and a shaft 110 extending proximally therefrom. Distal tip 105 of femoral guide 100 may be dimensioned and configured to have the same geometry and circumference as the desired resulting femoral tunnel. In this manner, distal tip 105 acts as a visual aid to assist the surgeon in determining proper tunnel placement by providing a direct visual confirmation of where the resulting femoral tunnel will be located. Alternatively, distal tip 105 may be formed with a semi-hemispherical cross-section (FIGS. 7B, 8B and 9B), or with an "unroofed" cross-section (FIGS. 7C, 8C, 9C and 10A-E) to aid in visualization.

Shaft 110 of femoral guide 100 is configured to be of such a length so as to at least extend (i) across the knee joint, (ii) across the length of the tibial tunnel and/or (iii) out of the medial portal. Shaft 110 and distal tip 105 are cannulated so as to accept (and thereby aim) a guidewire of an appropriate circumference, length and width.

In addition, the geometry of distal end 105 of femoral guide 100 may include (i) diametrically-opposed fingers 115 (FIGS. 9A-9C), and/or (ii) a distal projection 120 (FIGS.

10A-10E). Fingers 115 and/or projection 120 serve to reference the leading edge of the posterior cruciate ligament (PCL) and the posterior femoral cortex. Using the PCL as an anatomical reference enables a surgeon to set the femoral guide wire, and therefore the resulting femoral tunnel, in a position that better avoids any impingement of the PCL after the graft ligament has been placed in position. Such ACL/PCL impingement occurs when the femoral tunnel has been improperly positioned. In this manner, femoral guide 100 is configured to avoid any such ACL/PCL impingement, by using the PCL as an anatomical reference during formation of the femoral tunnel.

Figure 11:
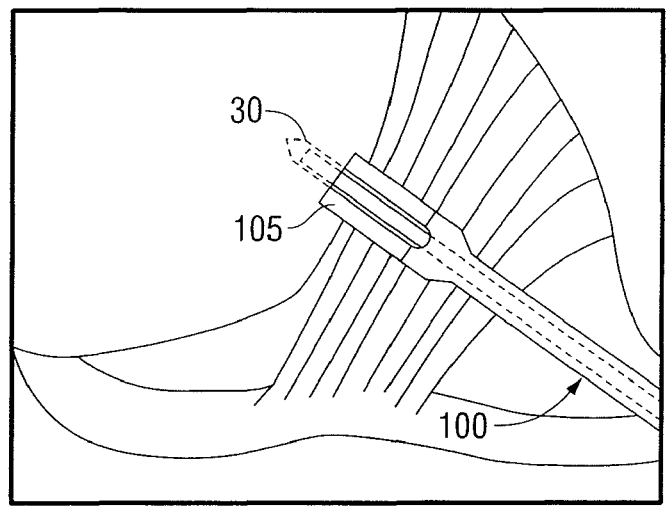
FIG. 11 is a partial cut-away view of a femoral guide according to an embodiment of the present disclosure being used in a medial portal approach.
Figure 12:
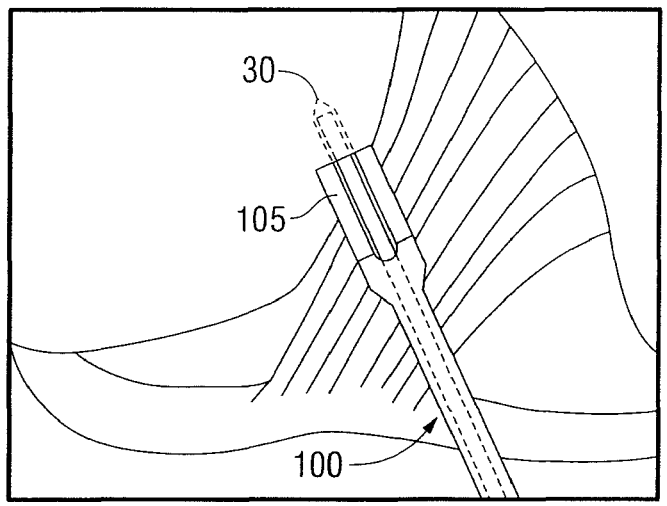
FIG. 12 is a partial cut-away view of a femoral guide according to an embodiment of the present disclosure being used in a trans-tibial approach.

As shown in FIG. 11, femoral guide 100 may be used in a medial portal approach with the knee in hyper-flexion, at approximately 120 degrees. However, it should be appreciated that femoral guide 100 may also be used with any ACL reconstruction approach, and with any angle of knee flexion. See, for example, FIG. 12, where femoral guide 100 is used during a traditional trans-tibial approach. Because of the size and/or configuration of distal end 105 of femoral guide 100, for use in the trans-tibial approach, femoral guide 100 may be halved, with one half for use with the right knee and the other half for use with the left knee.

Once the location of femoral tunnel 25 is identified by the surgeon with distal end 105 of femoral guide 100, guide wire 30 (FIG. 11) is extended through the cannulated shaft of elongated shaft 110 and into femur 15. Once guide wires 30 has been inserted into femur 15 to a desired depth, femoral guide 100 is then removed from about guide wire 30 and from the medial portal into the knee. A cannulated drill bit (not shown) is then received about guide wire 30 and through the medial portal to drill femoral tunnel 25.

Figure 13:
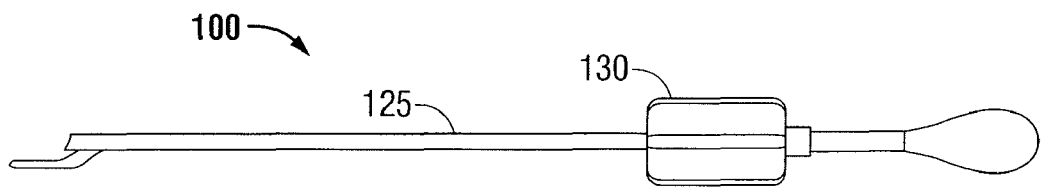
FIG. 13 is a side view of the proximal end of a femoral guide according to an embodiment of the present disclosure.

Looking next at FIG. 13, the proximal (or "butt") end 125 of femoral guide 100 is preferably provided with a docking port 130 to mate with a handle 135 to aid the surgeon in aiming the guide more easily and accurately. Handle 135 may be configured in any desired geometry so as to be ergonomically comfortable and/or to facilitate in the placement or holding of distal tip 105 in a particular position.

Femoral guide 100 provides surgeons with several significant improvements over prior art femoral guides. First, the distal portion of femoral guide 100 is configured (both in shape and diameter), to mirror that of the resulting tunnel and, therefore, the resulting graft. This gives the surgeon a visual "preview" or reference of the femoral tunnel prior to actually drilling the femoral tunnel. In addition, the distal shape of the femoral guide references the leading edge of the PCL's insertion onto the femur (i.e., the location where the PCL attaches to the femur) and places the resulting femoral tunnel in a position which avoids graft ACL/PCL impingement.

While some of the particular embodiments shown hereinabove have the cannulated shaft 220 defining a single guide wire lumen extending longitudinally therethrough, it should be recognized that the present invention may also include other embodiments in which the cannulated shaft 220 defines multiple guide wire lumen extending longitudinally therethrough. For example, FIG. 14 illustrates an example embodiment of a femoral tunnel positioning device 300 having an arrangement in which the cannulated shaft 220 defines multiple guide wire lumen extending longitudinally therethrough. Specifically, FIG. 14 illustrate an example embodiment of the present invention having an arrangement in which the cannulated shaft 220 defines a first guide wire lumen 260 and a second guide wire lumen 270 extending longitudinally therethrough.

Providing an arrangement in which the cannulated shaft 220 defines multiple guide wire lumen extending longitudinally therethrough may provide additional advantages as compared to embodiments in which the cannulated shaft 220 defines a single guide wire lumen extending longitudinally therethrough. For example, and as described hereinabove, in embodiments in which the cannulated shaft 220 defines a single guide wire lumen extending longitudinally therethrough, the cannulated shaft 220 is configured to receive a single size and/or shape of guide wire (while the figures provided illustrate the lumen having a generally circular cross-sectional shape, it should be recognized that any conceivable shape may be employed, e.g., triangular, square, octagonal, etc.). Turning briefly to FIG. 14A, a first guide wire lumen 260a defines a triangular cross-sectional shape and a second guide wire lumen 270a defines a square cross-sectional shape. Each of lumens 260a and 270a are also of different sizes. If a guide wire having a size and/or cross-sectional shape that is different from the lumen defined by the cannulated shaft 220 is attempted to be used, the cannulated shaft 220 may be unable to accommodate such irregular size and/or cross-sectional shape. In contrast, providing an arrangement in which the cannulated shaft 220 defines multiple guide wire lumen extending longitudinally therethrough may overcome some of these difficulties. For example, in embodiments in which the cannulated shaft 220 defines multiple guide wire lumen extending longitudinally therethrough, the cannulated shaft 220 may have lumen of differing sizes and/or shapes. In this way, the surgeon is not limited to using a single size and/or cross-sectional shape of guide wire, but rather may opt to utilize guide wires having various sizes and/or cross-sectional shapes.

In addition, in embodiments in which the cannulated shaft 220 defines a single guide wire lumen extending longitudinally therethrough, the centerline of the lumen of the cannulated shaft 220, and thus the centerline of the femoral tunnel when drilled, is typically configured to be vertically oriented relative to the distal offset projection 210. Such an arrangement may limit a surgeon to a single femoral tunnel position when the distal offset projection has been positioned against a surface of the femur, e.g., the posterior femoral notch. In contrast, having an arrangement in which the multiple guide wire lumen defined by the cannulated shaft 220 are arranged in side-by-side relationship relative to each other may enable a surgeon to select from various vertical alignments during the course of the surgical procedure. For example, if a surgeon determines, after the distal offset projection 210 has been positioned against a surface of the femur, e.g., the posterior femoral notch, that a guide wire placed through a first lumen 260 would provide a femoral tunnel position that is undesirable, the surgeon may then select to remove the guide wire from the first lumen 260 and to instead insert the guide wire through the second lumen 270 in order to achieve a femoral tunnel position that more desirable. Such adjustability may be advantageous for many reasons, e.g., to accommodate variations in different patients' anatomy, to avoid anatomical features within the patient's knee, to accommodate particular surgeon preferences with respect to the best tunnel positions, etc.

To aid the surgeon in utilizing an appropriate guide wire, the femoral tunnel positioning device 300 may provide indicia that provide an indication to the surgeon of the size and/or shape of the various lumens defined thereby.

While the above-described embodiment of the present invention includes an arrangement in which the multiple guide wire lumen defined by the cannulated shaft 220 are parallel to each other, it should be recognized that the present invention may also include other embodiments in which the multiple guide wire lumen defined by the cannulated shaft 220 are not parallel to each other. Furthermore, while the above-described embodiment of the present invention includes an arrangement in which the multiple guide wire lumen defined by the cannulated shaft 220 are arranged in side-by-side relationship relative to each other (e.g., whereby a distance between a centerline of each lumen and the distal offset projection is the same for each lumen), it should be recognized that the present invention may also include other embodiments in which the multiple guide wire lumen defined by the cannulated shaft 220 are not arranged in side-by-side relationship relative to each other. For example, FIG. 15 is a perspective view of a femoral tunnel positioning device 400 that illustrates an example embodiment of the present invention having an arrangement in which the multiple guide wire lumen defined by the cannulated shaft 220 are not arranged in side-by-side relationship relative to each other. Specifically, FIG. 15 illustrates an example embodiment of the present invention having an arrangement in which the multiple guide wire lumen defined by the cannulated shaft 220 are not arranged in side-by-side relationship relative to each other, but rather are arranged in vertical relationship relative to each other. In this manner, a distance between a centerline of the first lumen and the distal offset projection, and a distance between a centerline of the second lumen and the distal offset projection, may be different relative to each other. As shown in FIG. 15, the distance between the longitudinal axis of the first lumen 270 of the cannulated shaft 220 and the distal offset projection 210 is shown as $d_1$, while the distance between the longitudinal axis of the second lumen 260 of the cannulated shaft 220 and the distal offset projection 210 is shown as $d_2$, $d_2$ being greater than $d_1$. This increase in the distance may preferably be from 0 to about 4 mm, although any increase in this distance is contemplated.

Providing an arrangement in which the multiple guide wire lumen defined by the cannulated shaft 220 are arranged in vertical relationship relative to each other, e.g., such that each lumen is offset from the distal offset projection by a different amount, may provide additional advantages as compared to embodiments in which the cannulated shaft defines a single lumen extending longitudinally therethrough. For example, and similar to the advantages described hereinabove in connection with the embodiments of FIG. 14, having an arrangement in which the cannulated shaft 220 defines multiple guide wire lumen extending longitudinally therethrough may enable the use of different size and/or shape lumen, and thus a surgeon is not limited to using a single size and/or cross-sectional shape of guide wire. In addition, providing an arrangement in which the multiple guide wire lumen defined by the cannulated shaft 220 are arranged in vertical relationship relative to each other, e.g., such that each lumen is offset from the distal offset projection by a different amount, may provide additional advantages as compared to embodiments in which the multiple guide wire lumen defined by the cannulated shaft 220 are arranged in side-by-side relationship relative to each other and in which the cannulated shaft 220 defines a single lumen extending longitudinally therethrough. For example, in those embodiments in which the multiple guide wire lumen defined by the cannulated shaft 220 are arranged in side-by-side relationship relative to each other and in which the cannulated shaft 220 defines a single lumen extending longitudinally therethrough, the distance between a centerline of each lumen and the distal offset projection is the same for each lumen. Such an arrangement may limit a surgeon to a single femoral tunnel position when the distal offset projection has been positioned against a surface of the femur, e.g., the posterior femoral notch. In contrast, having an arrangement in which the multiple guide wire lumen defined by the cannulated shaft 220 are arranged in vertical relationship relative to each other may enable a surgeon to select from various offset distances during the course of the surgical procedure. For example, if a surgeon determines, after the distal offset projection 210 has been positioned against a surface of the femur, e.g., the posterior femoral notch, that a guide wire placed through a first lumen 260 is providing a femoral tunnel position that is undesirable (e.g., too posterior or too anterior), the surgeon may then select to remove the guide wire from the first lumen 260 and to instead insert the guide wire through the second lumen 270 in order to achieve a femoral tunnel position that more desirable. Such adjustability may be advantageous for many reasons, e.g., to accommodate variations in different patients' anatomy, to avoid anatomical features within the patient's knee, to accommodate particular surgeon preferences with respect to the best tunnel positions, etc.

While various of the above-described embodiments of the present invention include an arrangement in which the cannulated shaft 220 define two lumen extending longitudinally therethrough, it should be recognized that the present invention may also include other embodiments in which the cannulated shaft 220 defines more than two lumen extending longitudinally therethrough. For example, FIG. 16 is a perspective view of a femoral tunnel positioning device 500 that illustrates an example embodiment of the present invention having an arrangement in which the cannulated shaft 220 defines more than two, e.g., three, lumen extending longitudinally therethrough. Specifically, FIG. 16 illustrates an example embodiment of the present invention having an arrangement in which the cannulated shaft 220 defines a first lumen 260, a second lumen 270 and a third lumen 280 extending longitudinally therethrough. Although the present invention contemplates any desirable relative position of the various lumen, in the embodiment shown in FIG. 16, the first and second lumen 260, 270 are arranged in side-by-side relationship relative to each other, and in non-vertical relationship relative to the distal offset projection 210. The third lumen 28 is arranged in vertical relationship relative to the distal offset projection 210. In addition, the offset distances between the distal offset projection 210 and the first and second lumen 260, 270 are greater than the offset distance between the distal offset projection 210 and the third lumen 280. In this manner, the surgeon may have the ability to choose from various lumen, and thus from various femoral tunnel positions, during the course of a surgical procedure.

It should be understood that many additional changes in the details, materials, steps and arrangements of parts, which have been herein described and illustrated in order to explain the nature of the present disclosure, may be made by those skilled in the art while still remaining within the principles and scope of the disclosure.

What is claimed is:

1. A device for positioning a femoral tunnel during ACL reconstruction, the device comprising:
    an elongated shaft defining a longitudinal axis and at least two lumens extending longitudinally through the shaft along an axis parallel to the longitudinal axis, each lumen configured to receive a guide wire therethrough; and
    a distal offset projection extending distally from a distal end of the elongated shaft, wherein at least a portion of the distal offset projection is laterally spaced from and extends parallel to the longitudinal axis.

2. The device of claim 1, wherein the at least two lumen include a first lumen and a second lumen.

3. The device of claim 2, wherein the first lumen and the second lumen are arranged side-by-side relative to each other.

4. The device of claim 2, wherein a centerline of the first lumen is disposed at a distance from the distal offset projection that is equal to a distance between a centerline of the second lumen and the distal offset projection.

5. The device of claim 2, wherein the first lumen and the second lumen are arranged vertically relative to each other.

6. The device of claim 2, wherein a centerline of the first lumen is disposed at a distance $d_1$ from the distal offset projection that is not equal to a distance $d_2$ between a centerline of the second lumen and the distal offset projection.

7. The device of claim 6, wherein the difference between distance $d_1$ and distance $d_2$ is in the range from 0 to about 4 mm.

8. The device of claim 2, wherein the first lumen has a size that is different from a size of the second lumen.

9. The device of claim 2, wherein the first lumen has a cross-sectional shape that is different from a cross-sectional shape of the second lumen.

10. The device of claim 2, wherein the shaft defines a third lumen.

* * * * *